US011857453B2

(12) United States Patent
Granet et al.

(10) Patent No.: US 11,857,453 B2
(45) Date of Patent: *Jan. 2, 2024

(54) OSTOMY APPLIANCE

(71) Applicant: Sanguine Technology, LLC, Dunmore, PA (US)

(72) Inventors: Rosemary Granet, Scranton, PA (US); Paul Jason Granet, Scranton, PA (US); Gregory M. Murphy, Davidsonville, MD (US)

(73) Assignee: Sanguine Technology, LLC, Scranton, PA (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/480,768

(22) Filed: Sep. 21, 2021

(65) Prior Publication Data

US 2022/0000653 A1   Jan. 6, 2022

Related U.S. Application Data

(63) Continuation of application No. 16/849,909, filed on Apr. 15, 2020, now Pat. No. 11,129,744.

(Continued)

(51) Int. Cl.
*A61F 5/44* (2006.01)
*A61F 5/448* (2006.01)

(Continued)

(52) U.S. Cl.
CPC ............ *A61F 5/4404* (2013.01); *A61F 5/448* (2013.01); *A61B 46/00* (2016.02);
(Continued)

(58) Field of Classification Search
CPC .......... A61F 5/445; A61F 5/443; A61F 5/448; A61F 5/4404; A61F 2013/0057; A61F 2013/00978; A61F 2005/4483; A61F 5/44; A61M 1/915; A61M 27/00; A61M 1/90; A61M 1/916; A61M 1/984; B65D 41/16; B65D 41/165; B65D 41/17; B65D 41/18;
(Continued)

(56) References Cited

U.S. PATENT DOCUMENTS 3,980,213 A * 9/1976 Ramsay ............... B65D 47/127
222/570
5,834,009 A * 11/1998 Sawers ............... A61F 13/0226
604/338

(Continued)

*Primary Examiner* — Adam Marcetich
(74) *Attorney, Agent, or Firm* — Landmark Intellectual Property Law, LLC; Gregory M Murphy (57) ABSTRACT

In general, the present invention is directed to systems and methods for providing ostomy faceplates in proximity to negative pressure wound devices. This may be achieved, for example through the use of an ostomy appliance or faceplate with a non-circular flange for attachment of a bag or pouch. In accordance with some embodiments, this non-circular flange may be substantially "D"-shaped, and/or have at least one substantially straight edge. In some embodiments, the ostomy faceplate may itself be noncircular and/or "D"-shaped; may include a cutting guide for cutting materials (Continued)

used with an NPWD; may contain an asymmetrically located aperture; and/or may comprise one or more tapered edges.

7 Claims, 11 Drawing Sheets

Related U.S. Application Data

(60) Provisional application No. 62/871,670, filed on Jul. 8, 2019.

(51) Int. Cl.
*A61B 90/00* (2016.01)
*A61F 13/00* (2006.01)
*A61B 46/00* (2016.01)
*A61M 1/00* (2006.01)

(52) U.S. Cl.
CPC ............ *A61B 2090/037* (2016.02); *A61F 2013/00978* (2013.01); *A61M 1/90* (2021.05)

(58) Field of Classification Search
CPC ...... B65D 41/46; B65D 41/465; B65D 41/47; B65D 41/48; B65D 41/485; B65D 43/0204; B65D 43/0206; B65D 43/0208; B65D 43/021; B65D 43/0212; B65D 45/30; B65D 47/127
See application file for complete search history.

(56) References Cited

U.S. PATENT DOCUMENTS

| | | | |
|---|---|---|---|
| 6,537,261 B1 * | 3/2003 | Steer | A61F 5/448 604/342 |
| 7,891,514 B1 * | 2/2011 | Walsh | B65D 43/0212 220/780 |
| 9,204,990 B1 * | 12/2015 | Berven | A61F 5/443 |
| 9,750,633 B1 * | 9/2017 | Follenius | A61F 5/443 |
| 11,129,744 B2 * | 9/2021 | Granet | A61F 5/4404 |
| 2003/0015532 A1 * | 1/2003 | Rickman | E04F 21/00 220/780 |
| 2011/0137271 A1 * | 6/2011 | Andresen | A61F 13/023 604/319 |
| 2011/0166539 A1 * | 7/2011 | Eakin | A61F 5/445 604/339 |
| 2011/0278253 A1 * | 11/2011 | Goodall | B65D 41/0414 215/200 |
| 2012/0123363 A1 * | 5/2012 | Grum-Schwensen | A61F 5/448 604/342 |
| 2012/0253302 A1 * | 10/2012 | Corley | A61M 1/86 604/319 |
| 2018/0289185 A1 * | 10/2018 | Oakes | B65D 21/0223 |
| 2020/0253777 A1 * | 8/2020 | Jones | A61F 5/443 |
| 2021/0161725 A1 * | 6/2021 | Edwards | A61F 13/0216 |
| 2022/0168131 A1 * | 6/2022 | Heckler | A61F 5/443 |

* cited by examiner

Figure 1

Prior Art

OSTOMY APPLIANCE

RELATED APPLICATIONS

This application is a continuation of and claims priority to U.S. Non-Provisional Utility patent application Ser. No. 16/849,909 filed on 15 Apr. 2020 entitled "Systems and Methods for Providing Ostomy Faceplates in Close Proximity with Negative Pressure Wound Devices", which in turn claims priority to U.S. Provisional Patent Application No. 62/871,670, filed on 8 Jul. 2019 and entitled "Ostomy Appliance," each of which is incorporated by reference herein in its entirety.

BACKGROUND

Emergency surgery may result in both an ostomy (such as an ileostomy or a colostomy) and a surgical wound. Ileostomies (stomas made from the last portion of the small intestine) are generally placed in the lower right quadrant of a patient's abdominal wall below the level of the umbilicus but above the level of the pubic hair. Colostomies (stomas made from part of the large intestine) are generally placed in the lower left quadrant of the abdomen, although they can be placed in other locations. However, the site selection of an ostomy is often restricted, as stomas should be sited within margins of the rectus abdominal muscle, which runs vertically and in front of the abdomen. Placing a stoma within the margins of this muscle may help prevent later complications, such as parastomal hernias.

To seal an ostomy faceplate against a patient's skin, a flat surface of two (2) to three (3) inches circumferentially from the base of the stoma is recommended.

Emergency abdominal surgery generally requires and results in surgical wounds. To reduce the risk of developing a wound infection after skin closing—and in situations where bacteria or fecal matter may cause intra-abdominal contamination—many surgeons utilize an negative pressure wound device (NPWD) that promotes healing by secondary intention. It is known in the art to utilize NPWDs for the treatment of open wounds. For example, Kinetic Concepts, Inc. of San Antonio, Texas markets and sells a Vacuum Assisted Closure®—or V.A.C.® product line that typically involves mechanical-like contraction of a wound with simultaneous removal of excess fluid, often accomplished by using a polymer foam and occlusive drape dressing in communication with a negative pressure source. Similarly, Smith & Nephew PLC of London, England provides NPWDs, such as the PICO® and RENASYS® devices that utilize a silicone adhesive dressing that purportedly promotes healing and reduces dressing changes.

In order for any NPWD to work properly, a sufficient seal must be made over the patient's wound. Failure to provide a proper seal may result in failure to promote proper healing or in the NPWD's drawing unwanted fluids and material into the open and/or healing wound.

Unfortunately, patients who undergo emergency abdominal surgery may often have a fecal diversion strategy employed as part of care. Typically, this includes mobilizing a segment of a bowl through a separate incision in the abdominal wall, creating a fecal or urinary stoma, through which the patient may eliminate waste into a container attached to their abdomen. This container is typically a bag or pouch that may be attached to the body around the stoma by a faceplate or wafer of bioadhesive material. This faceplate or wafer may protect the peristomal skin from stomal effluent, preventing infection, pain, and/or other complications.

However, such stomas are often located proximate to a surgical wound. A short distance—which may be as little as a few centimeters—between the surgical wound and the ostomy opening may interfere with successful deployment of NPWDs. This may often result in additional or excess resource utilization including suboptimal function of the NPWD, unplanned dressing changes, numerous health care provider visits (often in the middle of the night), abandonment NPWD therapy as well as increased patient discomfort or distress.

Accordingly, proper sealing of the NPWD is highly desirable to prevent any effluent from the ostomy from being drawn into the wound. However, the shape and size of existing ostomy appliances or face plates are not suitable to be used when an abdominal wound is nearby and often interfere with NPWD placement or use.

Accordingly, it is desirable to provide an ostomy appliance that can be used in synergetic conjunction with an NPWD which may enable a patient to receive full benefit from NPWD therapy while minimizing additional resource utilization to achieve this end.

For example, it is frequently difficult to locate an ostomy appliance or faceplate in direct proximity with a drape used in an NPWD. Accordingly, it is desirable to provide an ostomy appliance that can be used to locate an NPWD as close to the ostomy appliance as possible. Similarly, it is desirable to have an ostomy appliance configured to accept an overlapping drape of an NPWD in a manner so as to maintain efficacy of both mechanisms.

In addition to the aforementioned difficulties, when an ostomy and a surgical wound are in proximity, the ostomy bag or pouch often falls over the surgical wound. This can cause discomfort, and make it more difficult for healthcare providers to check and examine the surgical wound properly. Accordingly, it is desirable to have an ostomy pouch or bag that is configured—through the bag or through the ostomy faceplate—to fall to the side opposite of a surgical wound.

SUMMARY OF THE INVENTION

Some aspects of the present invention, in accordance with some embodiments, may comprise ostomy appliance or faceplate with a non-circular flange for attachment of a bag or pouch.

Some aspects of the present invention, in accordance with some embodiments, may include additional features that may include: a substantially "D"-shaped flange; a non-circular flange having at least one substantially straight edge; an ostomy appliance or faceplate being noncircular and/or substantially "D"-shaped; a cutting guide disposed on the ostomy appliance or faceplate; a cutting guide that may be used to guide a cutting device when cutting drape or bandage material, for example drape or bandage material used with an NPWD; a cutting guide that may comprise a channel or groove; a cutting guide that may comprise one or more protrusions; a tapered edge on the ostomy appliance or faceplate; the tapered edge being disposed on the substantially straight part of a "D" shape; an ostomy appliance or faceplate comprised of an impermeable (or substantially impermeable, vapor permeable, etc.) material; a flange for attachment of a bag or pouch on an ostomy appliance or faceplate being disposed in an angular position, relative to a bottom surface of the ostomy appliance or faceplate; attachment devices for attaching a bag or pouch to the ostomy appliance or faceplate; and/or an asymmetrically located aperture within the faceplate/flange to minimize the space between the edge of the faceplate/flange and the ostomy itself.

Some aspects of the present invention, in accordance with some embodiments, may comprise a non-circular ostomy appliance including the following: a non-circular faceplate; a non-circular flange for attachment of a bag or pouch, the non-circular flange having at least one substantially straight edge; and a cutting guide for guiding a cutting device when cutting materials used with an NPWD, the cutting guide disposed co-linearly with the substantially straight edge.

Some aspects of the present invention, in accordance with some embodiments, may include additional features such as: a non-circular ostomy appliance having at least one substantially straight and tapered edge; an aperture configured to receive a stoma; an aperture located asymmetrically, the aperture being located within the flange; one or more lines of weakness disposed within the flange, such lines of weakness being used to remove a portion of the non-circular ostomy appliance or faceplate to form an aperture; a cutting guide for guiding a cutting device; a cutting guide to guide a cutting device while cutting material used with an NPWD; and/or a cutting guide that may comprise a channel or groove in the ostomy appliance or faceplate, or one or more protrusions.

Some aspects of the present invention, in accordance with some embodiments, may include an ostomy appliance or faceplate comprising a substantially planar surface and a flange, wherein at least a portion of the planar surface outside of the flange is removable.

Some aspects of the present invention, in accordance with some embodiments, may include an ostomy appliance or faceplate comprising a substantially planar surface with a thickness having a substantially straight edge, wherein substantially planar edge comprises a tapered edge, reducing the thickness of the substantially planar surface.

Some aspects of the present invention, in accordance with some embodiments, may include an ostomy appliance or faceplate configured to direct an ostomy bag or pouch attached thereto to a specific side of the ostomy appliance or faceplate.

These and other aspects will become apparent from the following description of the invention together with the following drawings, although variations and modifications may be effectuated without departing from the scope of the novel concepts of the invention.

BRIEF DESCRIPTION OF THE DRAWINGS

The present invention can be more fully understood by reading the following detailed description together with the accompanying drawings, in which like reference indicators are used to designate like elements. The accompanying figures depict certain illustrative embodiments and may aid in understanding the following detailed description. Before any embodiment of the invention is explained in detail, it is to be understood that the invention is not limited in its application to the details of construction and the arrangements of components set forth in the following description or illustrated in the drawings. The embodiments depicted are to be understood as exemplary and in no way limiting of the overall scope of the invention. Also, it is to be understood that the phraseology and terminology used herein is for the purpose of description and should not be regarded as limiting. The detailed description will make reference to the following figures, in which.

Before any embodiment of the invention is explained in detail, it is to be understood that the present invention is not limited in its application to the details of construction and the arrangements of components set forth in the following description or illustrated in the drawings. The present invention is capable of other embodiments and of being practiced or being carried out in various ways. Also, it is to be understood that the phraseology and terminology used herein is for the purpose of description and should not be regarded as limiting.

DETAILED DESCRIPTION

The matters exemplified in this description are provided to assist in a comprehensive understanding of various exemplary embodiments disclosed with reference to the accompanying figures. Accordingly, those of ordinary skill in the art will recognize that various changes and modifications of the exemplary embodiments described herein can be made without departing from the spirit and scope of the claimed invention. Descriptions of well-known functions and constructions are omitted for clarity and conciseness. Moreover, as used herein, the singular may be interpreted in the plural, and alternately, any term in the plural may be interpreted to be in the singular.

In general, the present invention is directed to the systems and methods of an improved ostomy appliance. Specifically, the present invention is directed to ostomy faceplates that are specifically configured for interactions with NPWDs.

The present invention sets forth an ostomy appliance and/or system that may include one or more of several features, including but not limited to the following: having a straight edge that may be aligned with a drape or other component of an NPWD; one or more channels for cutting drape material; one or more protrusions or rails for cutting drape material; a "D"-shaped ostomy appliance; a "D"-shaped flange for attaching an ostomy bag or pouch thereto; a tapered edge to facilitate overlapping by a drape material or other component of an NPWD; an ostomy appliance with an asymmetric and/or non-centered aperture for the stoma; an asymmetric ostomy bag or pouch configured to hang to the non-wounded side; attachment devices for an ostomy bag or pouch; and/or a breakaway or sump to reduce or prevent any stoma effluent from being drawn into the wound by an NPWD.

In accordance with some embodiments (and as discussed in greater detail below), the design may comprise a straight edge as part of ostomy faceplate, a "D"-shaped flange and an asymmetric effluent bag that may not encroach towards the midline. There may be a channel in the faceplate so that an organized straight cut of the impermeable (or substantially impermeable, vapor permeable, etc.) negative pressure bandage may be made just prior to it becoming enmeshed with the effluent bag. The straighter end of the faceplate (closest to wound) may include a tapered end in order to facilitate an adequate seal with the negative pressure bandage. The ostomy appliance may also have an impermeable (or substantially impermeable, vapor permeable, etc.) bandage surrounding the faceplate that may be compatible with one or more types of NPWD.

The bag of the ostomy appliance itself may also comprise a venting/sump system and/or snaps. More specifically, in accordance with some embodiments of the present invention, there may be a venting/sump system that may prevent the occasional complication of effluent being drawn into the wound by negative pressure, such as a break-away flap to prevent reversed flow. Additionally, in accordance with some embodiments, snaps may be included. For example, snaps (or other attachment devices, including but not limited mechanical attachment (hook-and-loop, zippers, latches, threaded connections, etc.), magnetic attachment, or any other type of suitable attachment) may be positioned to assist in securing the asymmetric bag to the faceplate. Positions of the snaps may vary. The male portion of the snap may be embedded in the faceplate and the female portion may be embedded on the bag, or vice versa. In accordance with some embodiments, other attachment devices may be embedded or attached to the faceplate and/or bag or may be attachable to a faceplate and/or bag so that other bags may be utilized.

Figure 1:
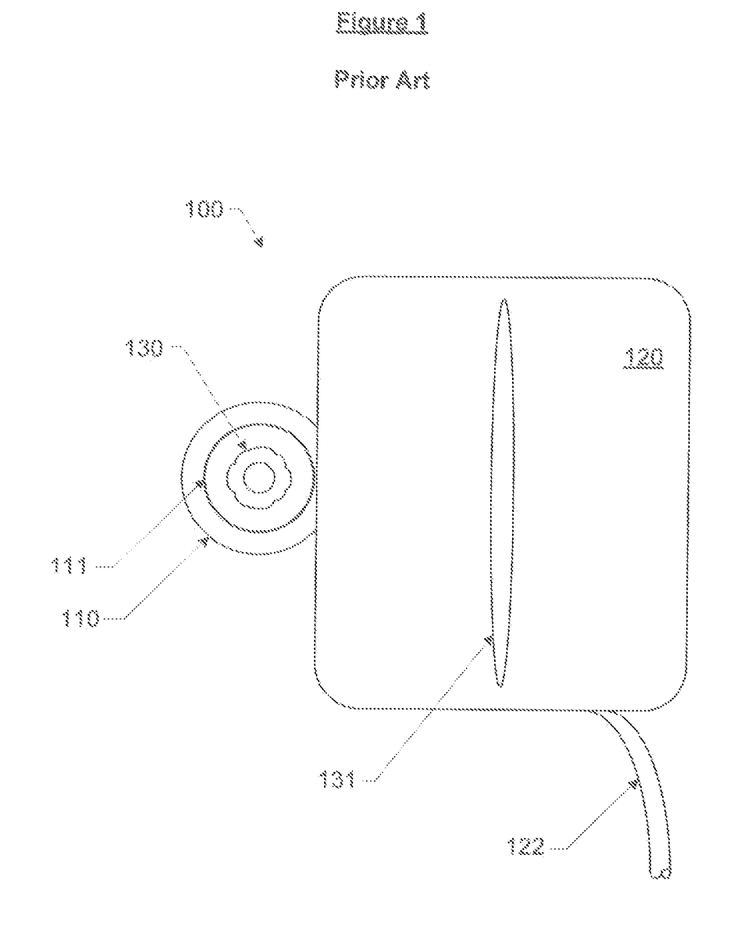
FIG. 1 illustrates a typical interaction between an ostomy appliance and an NPWD as often seen in the prior art.

With reference to FIG. 1, a prior art overlapping system 100 will be discussed. System 100 shows the use of an ostomy appliance 110 and a NPWD 120. Note that the NPWD 120 overlaps a portion of the ostomy appliance 110, due to the proximity between the stoma 130 and the wound 131. The ostomy appliance 110 is substantially round and may be centered over and substantially concentric with the stoma 130. The ostomy appliance may further include a round flange 111 for the attachment of a bag or pouch (not shown). The NPWD 120 may comprise a drape or dressing 121 that may be positioned over the wound 120, and may include conduit or tubing 122 to a negative pressure device, such as a vacuum system.

It can be seen from the prior art shown in FIG. 1 that when wounds are near or adjacent to an ostomy, there can be unintended interference between the ostomy appliance and the NPWD.

Figure 2:
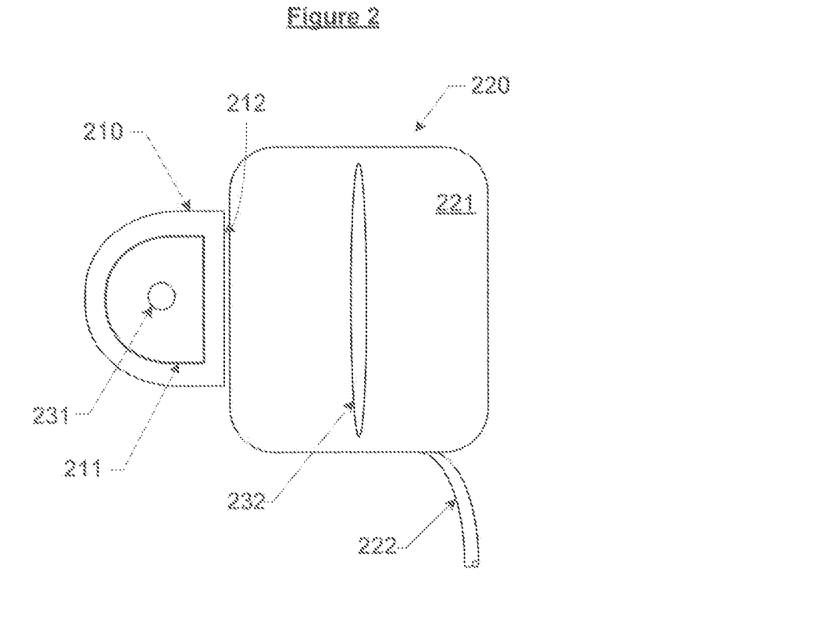
FIG. 2 depicts an exemplary "D"-shaped ostomy appliance with "D"-shaped flange, in accordance with some embodiments of the present invention.

With reference to FIG. 2, an exemplary "D"-shaped ostomy appliance with "D"-shaped flange, in accordance with some embodiments of the present invention will now be discussed. FIG. 2 illustrates a "D"-shaped ostomy appliance 210 which may include a flange 211 for the attachment of a bag or pouch and may be located over a stoma 231. The "D"-shaped ostomy appliance 210 may include a straight edge 212, which may be positioned such that there is little or no interference with an NPWD 220. The NPWD 220 may be positioned over a wound 232 and may comprise a drape material 221 with conduit or tubing 222 connected to a negative pressure device (not shown). It can be seen that the straight edge of the ostomy appliance permits both mechanisms of the NPWD and ostomy appliance to each be independently effective without interference from the other.

Figure 3:
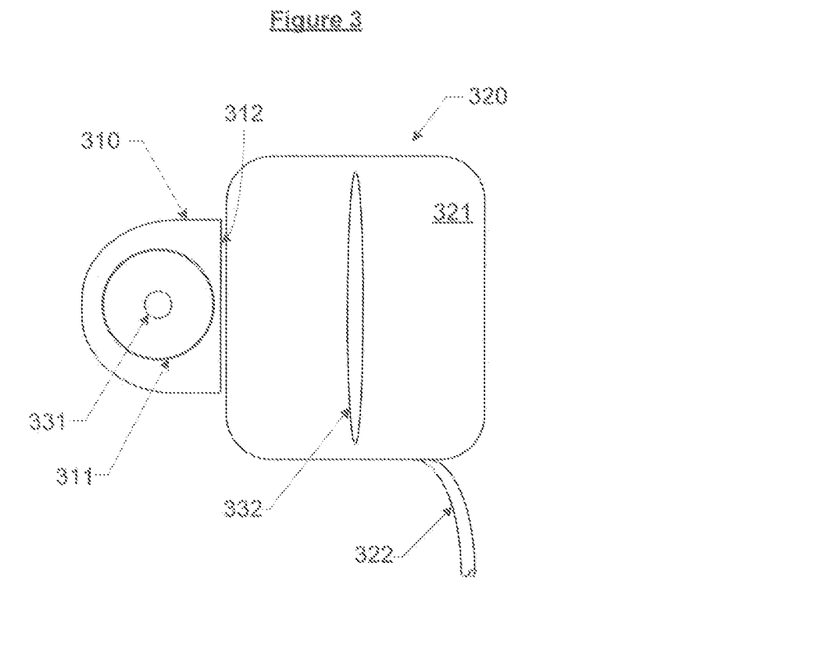
FIG. 3 depicts an exemplary "D"-shaped ostomy appliance with a typical round flange, in accordance with some embodiments of the present invention.

It is also contemplated that the ostomy appliance may be "D"-shaped but may maintain a circular or substantially circular flange. With reference to FIG. 3, an ostomy appliance 310 may include a straight edge 312 but may include a traditional and/or standard round flange 311, which may be substantially centered over a stoma 331. In this manner, standard ostomy bags or pouches may be used to attach to the flange 311.

Note that while the present invention uses terms such as "D"-shaped, this specific shape is not required. Rather, it is the straighter edge of the ostomy appliance that may be located adjacent or even abutting the NPWD that provides simultaneous use without unwanted or undesirable interference. Accordingly, the present invention should not be limited to this exact arrangement.

Figure 4:
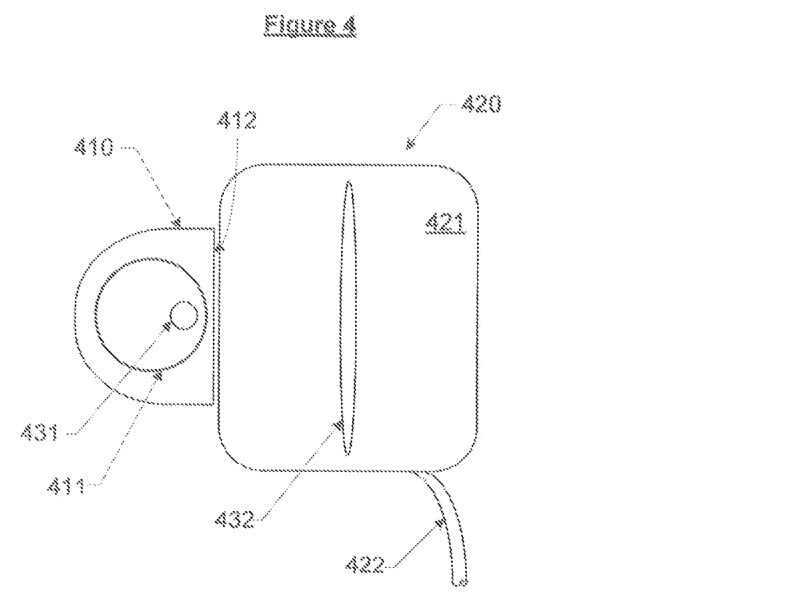
FIG. 4 illustrates an exemplary "D"-shaped ostomy appliance with a round flange, and an asymmetrically located stoma, in accordance with some embodiments of the present invention.

It is further contemplated that the location of the ostomy appliance may not be centered upon a stoma. With reference to FIG. 4 an ostomy appliance 410 may include a flange 411 and a straight edge 412. The straight edge 412 may be positioned proximate to an NPWD 420, which may in turn comprise a drape 421 positioned over a wound 432 with conduit or tubing 422 connected to a negative pressure device (not shown). Because of proximity between the stoma 431 and wound 432, the ostomy appliance 410 may be positioned as close to the stoma—and as far away from the wound—as possible. This may result in the stoma's being positioned in a nonconcentric location. Note that while this may not be ideal from a drainage perspective, once the wound adequately heals where an NPWD is unnecessary an ostomy faceplate may be positioned more centrally over the stoma.

Figure 5:
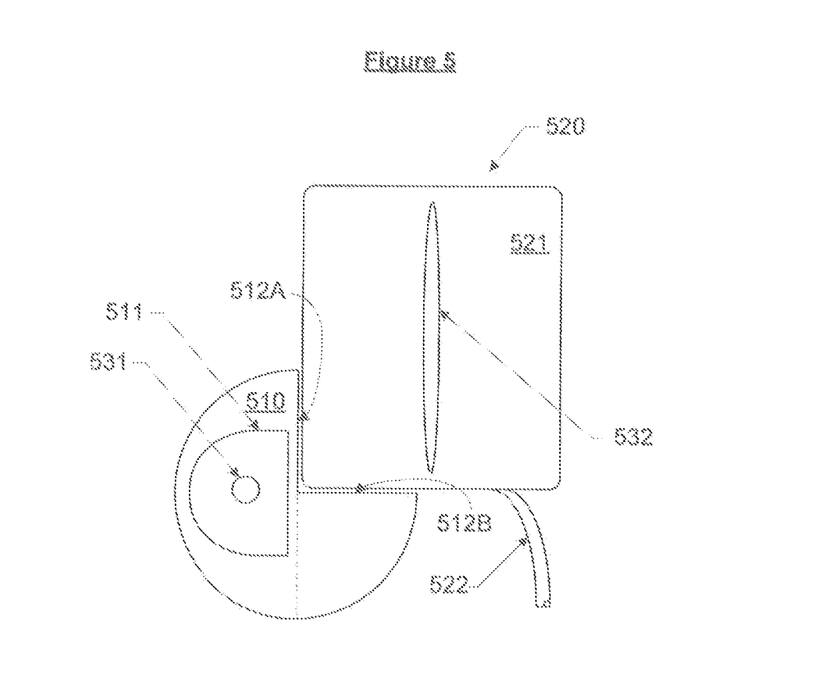
FIG. 5 illustrates an exemplary "D"-shaped ostomy appliance with a "D"-shaped flange, and an asymmetrically located stoma, in accordance with some embodiments of the present invention.

With reference to FIG. 5, an exemplary ostomy faceplate 510 with a cut-out is shown. Ostomy faceplate 510 may again include a flange 511 for attachment to a bag or pouch. The ostomy faceplate 510 may further include two (2) straight edges 512A, 512B which may be used to position the faceplate 510 as close to drape material 521 for an NPWD 520 as possible. Again, the NPWD 520 may cover a wound 532 and may be attached to a negative pressure device (not shown) for generating negative pressure. Note that while the ostomy faceplate 510 is shown with a quarter removed, it is anticipated that various designs, arrangements, or configurations may be utilized to achieve close placement of the ostomy appliance to the NPWD or its associated drape or dressing.

Also note that while the ostomy appliance 510 is shown with approximately one quarter removed, it is also anticipated that the appliance 510 may include one or more lines of weakness 513, which may be used to remove portions of the faceplate. For example, the ostomy appliance 510 may be sold with a substantially circular or even rectangular shape but may include one or more lines of weakness 513. Lines of weakness 513 may be used to remove portions of the ostomy appliance or faceplate. For example, a substantially circular ostomy faceplate may include at least two lines of weakness. Lines of weakness may be substantially perpendicular to each other such that portions of the faceplate may be removed. To maintain a consistent flange for bag or pouch attachment, the flange may be asymmetrical (such as the illustrated "D" shape) or may be offset to one or more sides of the faceplate. In this manner, portions of the faceplate may be removed to allow for close placement to an NPWD.

In accordance with some embodiments of the present invention, an ostomy appliance or faceplate may include features to assist in cutting an NPWD drape or dressing—or indeed any proximate dressing. As discussed in greater detail below, such features may comprise a channel, one or more ridges or protrusions, joints or junctions to guide a cutting device, or other such alignment or guiding features.

Figure 6:
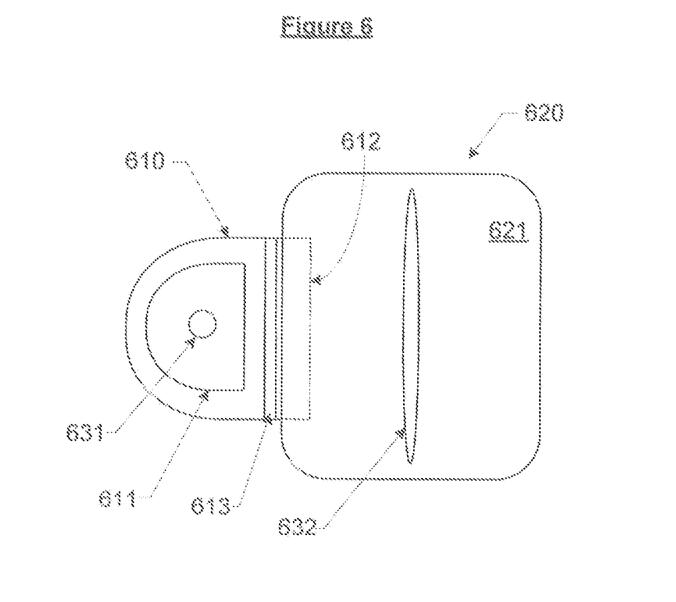
FIG. 6 depicts an exemplary ostomy appliance with channel, in accordance with some embodiments of the present invention.

With reference to FIG. 6 an ostomy appliance 610 is illustrated. Note that while ostomy appliance 610 is illustrated as being "D"-shaped, it may take various shapes as discussed above. Ostomy appliance 610 may comprise a flange 611, which is also illustrated as being "D"-shaped but may be in any other shape or configuration as discussed above. Adjacent or near the ostomy appliance 610 may be an NPWD 621. Negative pressure wound device 620 may include a drape or dressing 621, which may be attached a device that generates negative pressure, such as a vacuum (not shown). Ostomy appliance 621 may be positioned over or around stoma 631, while the NPWD 620 may be positioned over or around wound 632. Ostomy appliance 610 may further comprise a channel or groove 613. Channel or groove 613 may be made in any number of ways, such as by an indent in the surface of the ostomy appliance 610 or by one or more ridges or protrusions. In this manner the drape or dressing used with an NPWD can be cut as close as possible to the ostomy appliance.

As can be seen from FIG. 6, there may be some overlap where the drape or dressing 621 overlaps a portion of the ostomy appliance or faceplate 610. In accordance with some embodiments of the present invention, an ostomy appliance or faceplate may include features to assist sealing of drapes or dressings used with an NPWD. For example—and as discussed in greater detail below—one or more sides of the ostomy appliance or faceplate may taper from its usual thickness to a lesser thickness, providing a more gradual transition between a drape or dressing and an ostomy appliance, and thereby assisting in obtaining and maintaining a proper seal of the drape or dressing.

Figure 7:
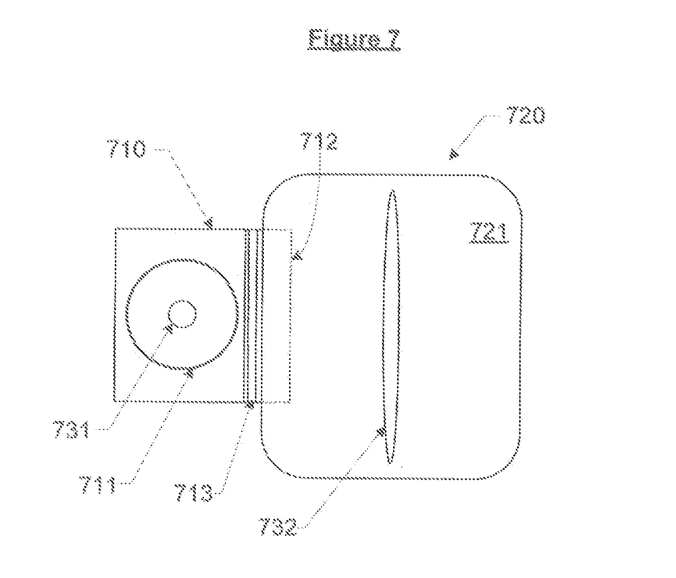
FIG. 7 illustrates an exemplary ostomy appliance and NPWD drape, in accordance with some embodiments of the present invention.

FIG. 7 illustrates a similar arrangement as shown in FIG. 6 above but illustrates the orientation of a channel in an ostomy appliance or faceplate 710 that is substantially square or rectangular. The ostomy appliance or faceplate 710 may include a flange 711 that may be round, "D"-shaped, square, or any other variation, and may further include a channel or guide 713 that may run substantially parallel or co-linear with edge 712. Drape or dressing 721 may be configured over and/or around wound 732, and (as discussed above) may overlap or abut a portion of the appliance or faceplate 710.

Figure 8:
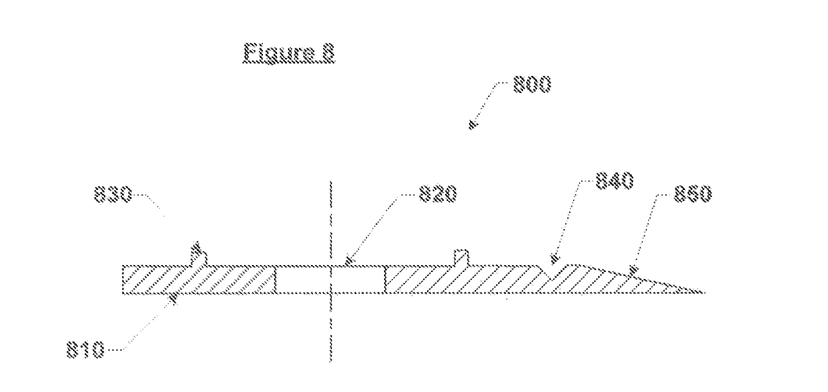
FIG. 8 depicts a cross-section of an exemplary ostomy appliance, in accordance with some embodiments of the present invention.

With reference to FIG. 8, a cross section of an ostomy appliance 800 in accordance with some embodiments of the present invention will now be discussed. Ostomy appliance 800 may include a faceplate 810, a hole or aperture 820 through which a stoma may protrude, a flange 830 (which may be in any size or shape sufficient to attach to an ostomy bag or pouch), a channel or groove 840, and a taper portion 850 proximate to the channel or groove 840.

Figure 9:
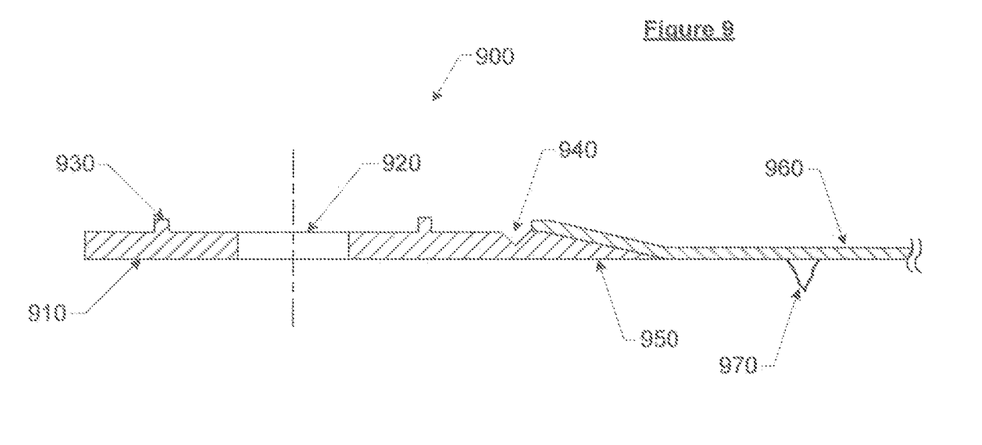
FIG. 9 depicts a cross section of an exemplary ostomy appliance and NPWD, in accordance with some embodiments of the present invention.

With reference to FIG. 9, interaction between an ostomy appliance 910 and a drape or dressing 960 for an NPWD will now be discussed. As illustrated above, an ostomy appliance 910 may include a hole or aperture 920 through which a stoma may protrude, a flange 930 (which may be in any size or shape sufficient to attach to an ostomy bag or pouch), a channel or groove 940, and a taper portion 950 proximate to the channel or groove 940. A drape or dressing 960 used in conjunction with an NPWD may be positioned over a wound 990 and may have a portion 970 extend over the taper portion 950 of the ostomy appliance 910. It can be seen that the drape or dressing 960 may extend up to channel or groove 940. During installation the channel or groove 940 may provide guidance so that an organized straight cut of an impermeable (or substantially impermeable, vapor permeable, etc.) negative pressure bandage or drape may be made.

Figure 10:
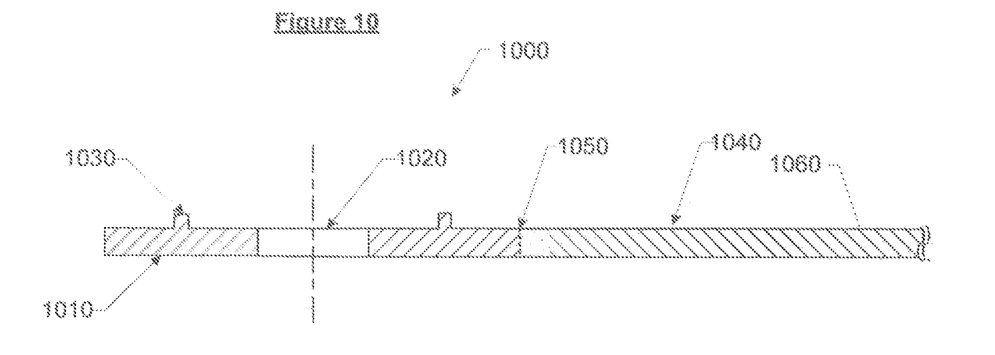
FIG. 10 illustrates a cross section of an exemplary ostomy appliance and NPWD, in accordance with some embodiments of the present invention.

It is contemplated that various other arrangements or interactions between an ostomy appliance and dressing or bandages for an NPWD may exist. For example, as illustrated in FIG. 10, it is contemplated that an ostomy appliance faceplate 1010 may comprise an impermeable material (or substantially impermeable, vapor permeable, etc.) and may be integrally connected to, or part of, a drape or bandage 1040 for an NPWD. The faceplate portion 1010 of the integral device 1000 may include an opening or aperture 1020 for a stoma and a flange 1030 for the connection of a bag or pouch. In accordance with some embodiments, the faceplate portion 1010 may be comprised of one material, while the drape portion 1040 may be comprised of a second material. For example, the faceplate portion 1010 may be made of a rigid material, while the drape portion 1040 may be made of a flexible material, typically used for bandages or drapes.

In accordance with some embodiments of the present invention, certain mechanisms, devices, or arrangements may be used to direct an ostomy bag or pouch to fall to a patient's side, away from a surgical (or other) wound. For example, as illustrated in FIG. 11, an ostomy faceplate or appliance 1110 may be configured to provide a typical aperture for a stoma 1120, but to have the flange for attachment of ostomy bags or pouches be positioned at an angle, such that while the flange lies in a single plane, one portion of the flange support 1160 is positioned further from the patient's skin (i.e., further in a Y axis), while another portion of the flange support 1170 is positioned closer to the patient's skin.

Figure 11:
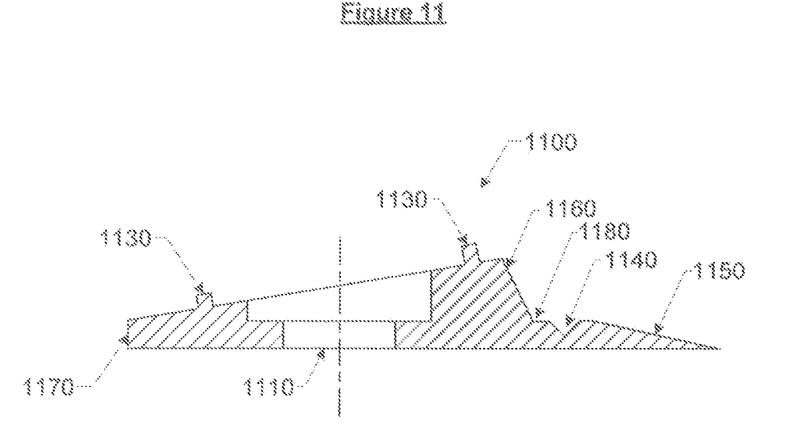
FIG. 11 depicts a cross section of an exemplary ostomy appliance in accordance with some embodiments of the present invention.

With continued reference to FIG. 11, a channel or groove 1140 may be positioned in the ostomy appliance 1110 to assist in cutting drape or other material associated with or used with an NPWD. Similarly, as discussed in greater detail above, the ostomy appliance 1110 may also comprise a tapered portion 1150 that may assist in creating a seal between drape material and the ostomy appliance 1110.

Note that in some alternatives the channel or groove 1140 may be omitted, as a surgeon may utilize the joint 1170 between the raised portion of the flange support 1160 and the other portions of the faceplate.

Figure 12:
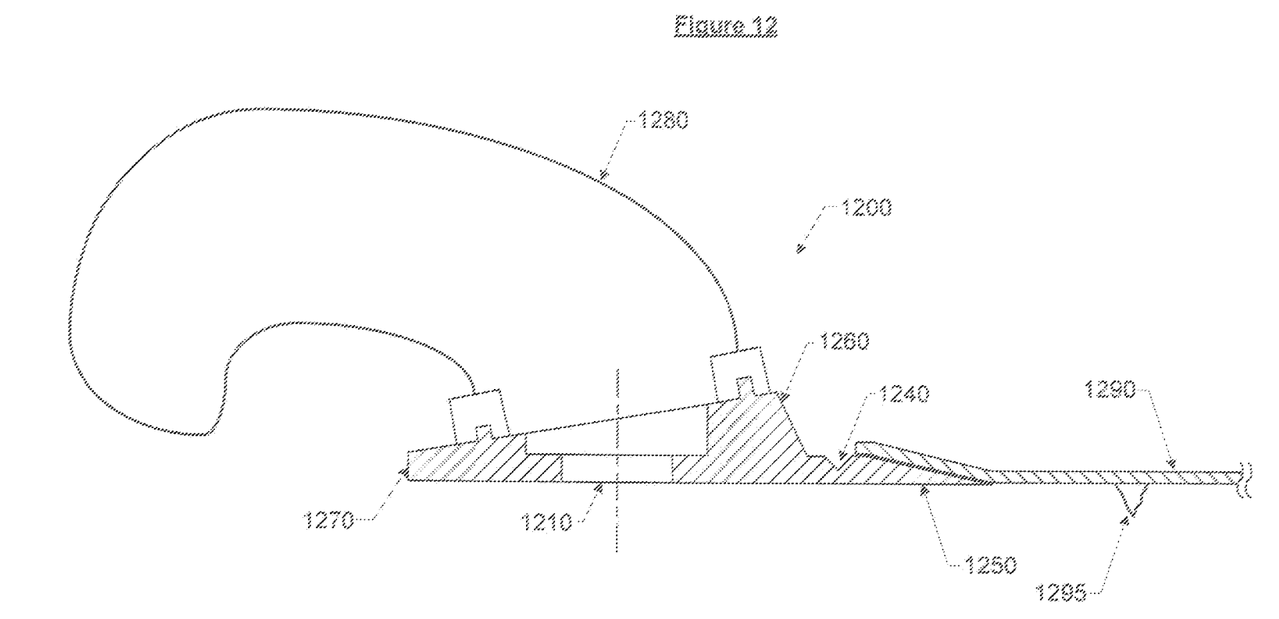
FIG. 12 illustrates a cross section of an exemplary ostomy appliance with attached bag or pouch and NPWD, in accordance with some embodiments of the present invention.

With reference to FIG. 12, the use of an angled ostomy appliance 1210 in conjunction with an ostomy bag or pouch 1280 is illustrated. Again, the ostomy appliance 1210 may include an opening or aperture 1220 for a stoma, a flange 1230 which may be positioned on an angle by resting on a first flange support portion 1260 that may be positioned further from a patient's skin than a second flange support 1270. The ostomy appliance 1210 may further comprise a channel or groove 1240 and a tapered portion 1250. During use, a drape or bandage 1290 of an NPWD may cover a wound 1295 and may extend up the tapered portion 1250 of the ostomy appliance.

Note that while the above discussions with reference to FIGS. 11 and 12 have discussed a first and second flange support, such supports are not necessarily distinct from one another. In other words, the flange itself may lie in a single plane, said plane being configured on an angle compared with the patient's skin surface. In a cross-section view, this may result in seeing a first flange support portion and a second flange support portion. However, this may present a single surface lying on an angle with a smooth transition from one portion to the next. The above language is included not to limit the device to two such portions or their arrangement, but to illustrate that an ostomy bag or pouch may be persuaded to lie in a certain direction by angling the flange and bag support.

Figure 13:
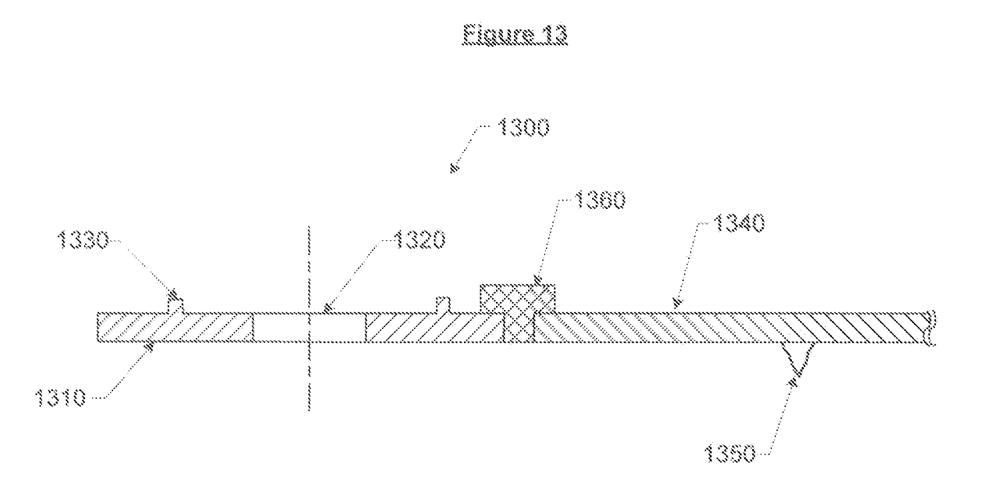
FIG. 13 depicts a cross section of an exemplary ostomy appliance and NPWD, in accordance with some embodiments of the present invention.

With reference to FIG. 13, interaction between an ostomy faceplate or appliance 1310 and a drape material 1340 for an NPWD will now be discussed. Again, ostomy faceplate 1310 may comprise an opening or aperture 1320 for a stoma and a flange 1330 for attachment of a bag or pouch. The flange may be of any shape, for example round, square, "D"-shaped, etc. The drape material 1340 may be positioned over a wound 1350. To prevent pressure communication between the drape material 1340 and the ostomy appliance 1310, a junction barrier 1360 may be utilized. Junction barrier 1360 may be comprised of an impermeable (or substantially impermeable, vapor permeable, etc.) material to prevent the negative pressure drawn by a negative pressure device (not shown) and applied under the drape material 1340 from drawing any effluent from the stoma, for example from around the flange 1330 (potentially due to a bag or pouch not being fully engaged, or a leaky seal therebetween), or from drawing effluent from under the ostomy faceplate 1310. This junction barrier 1360 may be, for example, "T" shaped, and may comprise adhesive under the arms of the "T" such that the junction barrier may attach to one or both of the ostomy faceplate 1310 and the drape material 1340.

Figure 14:
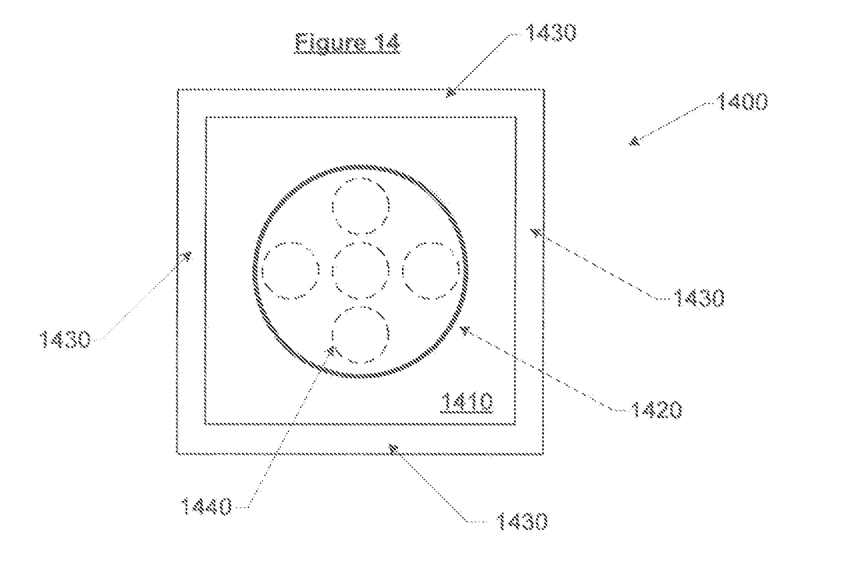
FIG. 14 illustrates an exemplary ostomy appliance, in accordance with some embodiments of the present invention.
Figure 15:
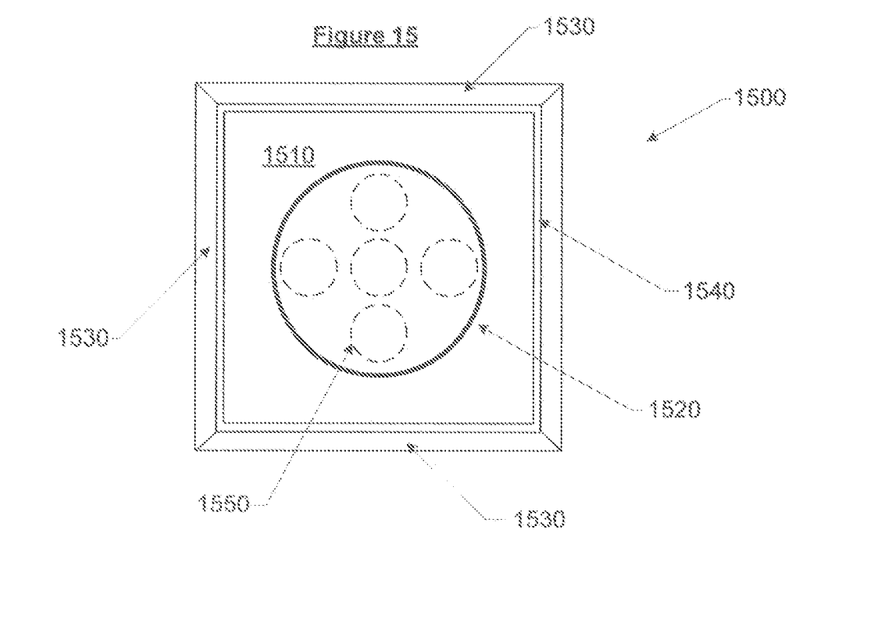
FIG. 15 illustrates an exemplary ostomy appliance, in accordance with some embodiments of the present invention.

With reference to FIG. 14, a top view of a quadrilateral shaped ostomy appliance 1400 will now be discussed. Ostomy appliance 1400 may comprise a faceplate 1410 that may include a flange 1420 and one or more tapered portions 1430. Within flange 1420 (which may be of any shape, such as round or "D"-shaped), there may be various lines of weakness 1440 such that an aperture for a stoma may be positioned within the flange 1430 in the most desirable location (based on the required location of the stoma and the surgeon's preference). Similar to FIG. 14, FIG. 15 illustrates an ostomy appliance 1500 that includes a flange 1520 and both tapered portions 1530 and a channel or groove 1540 that may be present on all edges of the faceplate 1510. Again, within flange 1520 there may be various lines of weakness 1550 such that an aperture for a stoma may be positioned within the flange 1530 in any number of locations.

Figure 16:
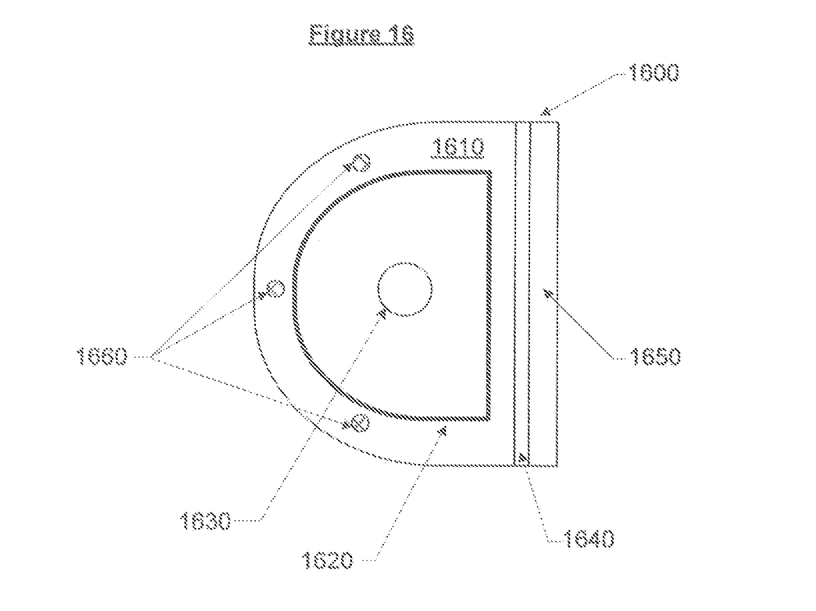
FIG. 16 illustrates an exemplary ostomy appliance with attachment devices, in accordance with some embodiments of the present invention.

With reference to FIG. 16, a "D"-shaped ostomy appliance 1600 will now be discussed. Ostomy appliance 1600 may comprise a faceplate 1610, a flange 1620, an aperture for a stoma 1630, a channel or groove 1640, and/or a tapered portion 1650, positioned along the straight edge of the "D" shape. Ostomy appliance 1600 may further comprise snaps, hooks, or other attachment devices 1660 in order to connect a bag or pouch to the ostomy appliance 1600. Such attachment devices 1660 are illustrated at the seven o'clock, nine o'clock and eleven o'clock positions, but may be present at any location upon the faceplate 1610.

Figure 17:
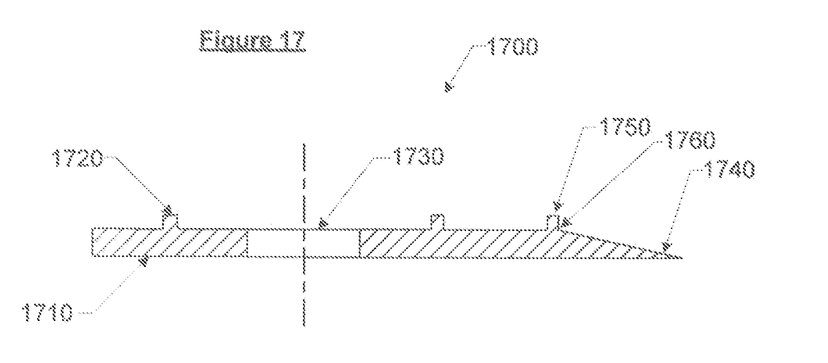
FIG. 17 depicts a cross section of an exemplary ostomy appliance, in accordance with some embodiments of the present invention.

With reference to FIG. 17, an ostomy appliance 1700 may comprise a faceplate 1710, a flange 1720, an aperture for a stoma 1730, a tapered portion 1740, and a cutting guide 1750. In this embodiment, rather than a full channel or groove, a protruding rail 1750 may be used to guide a surgeon's cutting device (for example, a knife, scalpel, scissors or scissor blade, etc.) in order to make a straight cut along the edge of the ostomy appliance 1700. For example, a surgeon may place the edge of a cutting device in the junction 1760 of the protruding rail and the tapered portion to guide the cutting device.

Figure 18:
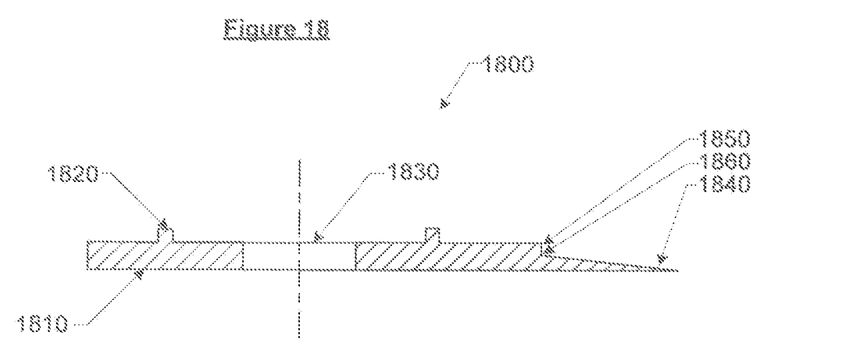
FIG. 18 depicts a cross section of an exemplary ostomy appliance, in accordance with some embodiments of the present invention.

Similar to FIG. 17, FIG. 18 illustrates an ostomy appliance 1800 that may comprise a faceplate 1810, a flange 1820, an aperture for a stoma 1830, and a tapered portion 1840. In this embodiment, however, the tapered portion steps up to the main body of the ostomy faceplate 1810 at step 1850. The junction 1860 between the tapered portion 1840 and the step 1850 may be used to guide a surgeon's cutting device. Note that in some embodiments, the thickness of the step 1850 may be comparable to the thickness of a drape used in an NPWD, so that upon installation there is a relatively smooth surface between the ostomy appliance and the drape.

Figure 19:
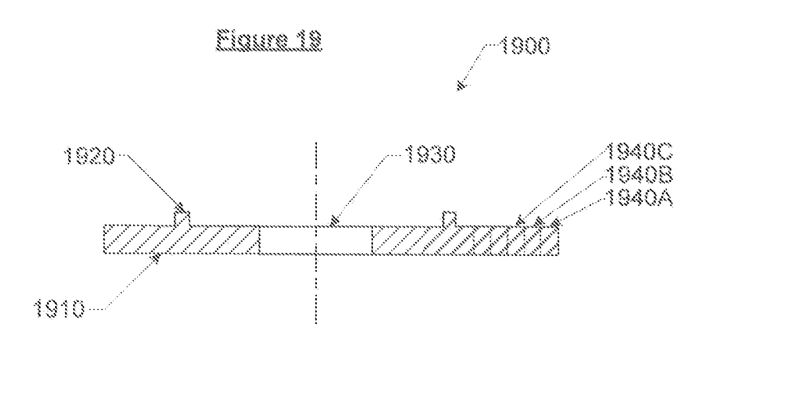
FIG. 19 depicts a cross section of an exemplary ostomy appliance, in accordance with some embodiments of the present invention.

With reference to FIG. 19, a different approach to placing an NPWD as close to an ostomy as possible is shown. Here, ostomy appliance 1900 may comprise faceplate 1910, flange 1920, and aperture for a stoma 1930. Ostomy faceplate 1910 may comprise one or more portions 1940 that are removable, joined by lines of weakness. In this manner, portions 1940A, 1940B, 1940C, etc., may be removed as necessary such that ostomy appliance 1910 may be placed as close as possible to an NPWD and/or its associated drape or bandage.

Figure 20:
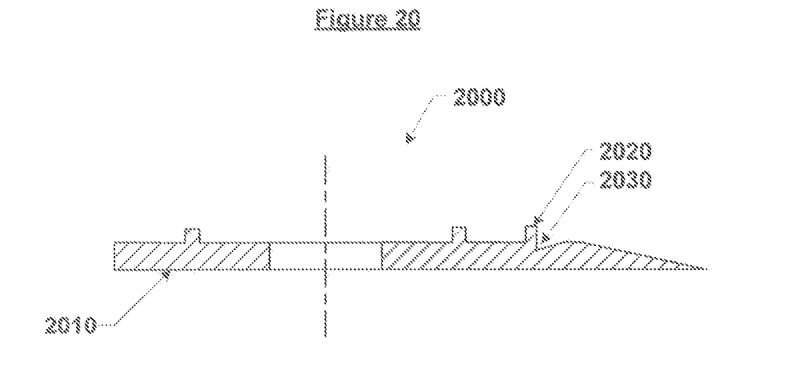
FIG. 20 depicts a cross section of an exemplary ostomy appliance, in accordance with some embodiments of the present invention.
Figure 21:
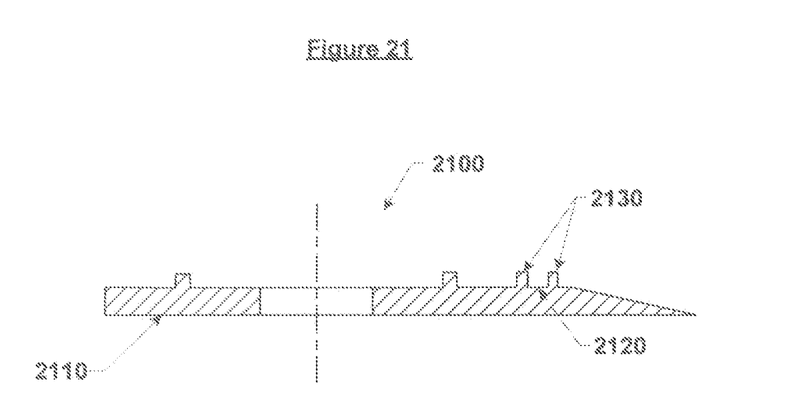
FIG. 21 depicts a cross section of an exemplary ostomy appliance, in accordance with some embodiments of the present invention.

FIGS. 20 and 21 show alternative embodiments to cutting guides. FIG. 20 illustrates a faceplate 2010 with combination of an extrusion 2020 and a channel, slot, or groove 2030. In this manner, the depth of the channel 2030 may be maintained deep enough to guide a cutting device, while not threatening the rigidity of the faceplate 2010. FIG. 21 illustrates an ostomy faceplate 2110 with a channel, slot, or groove 2120 formed between two protrusions 2130. This may also permit the presence of a channel or groove on the faceplate 2110 without jeopardizing the structure or structural rigidity of the faceplate 2110.

Note in accordance with some embodiments of the present invention, the ostomy bags or pouches that mate with or connect to flanges of the present invention may have a corresponding shape or attachment mechanism. In other words, it is anticipated that a "D"-shaped flange on an ostomy appliance or faceplate may require an ostomy bag or pouch with a corresponding mating "D"-shaped attachment device.

While the following discussion is exemplary, it is intended to provide background information into the installation and use of an improved ostomy appliance in conjunction with an NPWD. When a patient presents with both a wound and an ostomy, an ostomy appliance may first be installed over or around a stoma. When doing so, an ostomy appliance may have a preexisting aperture, or an aperture may be cut into the appliance. The ostomy appliance may be attached to the patient using adhesive typically attached to the bottom surface of an ostomy appliance.

During installation of an NPWD, a drape or bandage may be placed over a wound and may be cut as close to the ostomy device as possible, for example by using a cutting guide disposed at the edge of the ostomy appliance. In accordance with some embodiments, the edge of the ostomy appliance may be tapered such that the drape or bandage may overlap a small portion of the ostomy appliance but may be configured to maintain an adequate or proper seal. It is contemplated that the ostomy appliance—or the portion of the ostomy appliance anticipated to be overlapped by a drape or bandage—may be made of a non-permeable material, a hydrocolloid film, a drape with an acrylic adhesive coating and a silicone layer, etc.

It will be understood that the specific embodiments of the present invention shown and described herein are exemplary only. Numerous variations, changes, substitutions and equivalents will now occur to those skilled in the art without departing from the scope of the invention. Accordingly, it is intended that all subject matter described herein and shown in the accompanying drawings be regarded as illustrative only, and not in a limiting sense.

What is claimed is:

1. An ostomy appliance being a wafer, barrier, or faceplate, with a non-circular flange for mechanical attachment of a bag or pouch.

2. The ostomy appliance of claim 1, wherein the non-circular flange has at least one substantially straight edge.

3. The ostomy appliance of claim 1, wherein the ostomy appliance or faceplate is noncircular.

4. The ostomy appliance of claim 1, wherein the ostomy appliance or faceplate is comprised of an impermeable, substantially impermeable, or vapor permeable material.

5. The ostomy appliance of claim 1, further comprising an aperture, configured to receive a stoma.

6. The ostomy appliance of claim 5, wherein the aperture is located asymmetrically, the aperture being located within the flange.

7. An ostomy appliance being a wafer, barrier, or faceplate, comprising a non-circular flange with a substantially straight edge for attachment of a bag or pouch, the flange being a semi-rigid material that mechanically connects the bag or pouch to the appliance or faceplate.

* * * * *